US011933409B1

(12) United States Patent
Cyriac

(10) Patent No.: US 11,933,409 B1
(45) Date of Patent: Mar. 19, 2024

(54) INTEGRATED DIVERTER VALVE WITH DUAL GAS PATH FOR VENTILATOR AND ANESTHESIA SYSTEMS

(71) Applicant: GE Precision Healthcare LLC, Wauwatosa, WI (US)

(72) Inventor: Elvin Cyriac, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/072,150

(22) Filed: Nov. 30, 2022

(51) Int. Cl.
*F16K 11/044* (2006.01)
*A61M 16/20* (2006.01)
*F16K 15/06* (2006.01)

(52) U.S. Cl.
CPC .......... *F16K 11/044* (2013.01); *F16K 15/063* (2013.01); *A61M 16/208* (2013.01)

(58) Field of Classification Search
CPC .... A61M 16/08; A61M 16/20; A61M 16/201; Y10T 137/5109; Y10T 137/87965
USPC .................................................... 128/205.24
See application file for complete search history.

(56) References Cited

U.S. PATENT DOCUMENTS

| 309,260 | A | * | 12/1884 | Taylor | F16K 27/003 137/613 |
|---|---|---|---|---|---|
| 998,843 | A | * | 7/1911 | Dunn | F16K 27/003 237/40 |
| 3,176,705 | A | * | 4/1965 | Holmes | F16K 27/02 137/599.11 |
| 9,486,602 | B2 | * | 11/2016 | Allum | A61B 5/087 |
| 9,923,442 | B2 | | 3/2018 | Chalvignac | |
| 10,077,709 | B2 | | 9/2018 | Turner | |
| 11,471,638 | B2 | * | 10/2022 | Appareti | A61M 16/122 |
| 2013/0186394 | A1 | * | 7/2013 | Hallett | A61M 16/0057 128/205.24 |
| 2021/0310579 | A1 | * | 10/2021 | Maleki | A61M 39/24 |

* cited by examiner

*Primary Examiner* — Robert K Arundale

(57) ABSTRACT

A flow diversion valve, the flow diversion valve including: a valve housing having a first inlet, a second inlet, a first outlet, a second outlet, and an inner cavity; a float valve provided within the inner cavity of the valve housing; and a check valve provided on the float valve. The flow diversion valve having a first configuration in which the float valve is in a closed position to provide a first flow path from the first inlet to the first outlet. The flow diversion valve having a second configuration in which the float valve is in an open position to provide a second flow path from the first inlet through the second outlet and a third flow path from the second inlet to the first outlet.

20 Claims, 10 Drawing Sheets

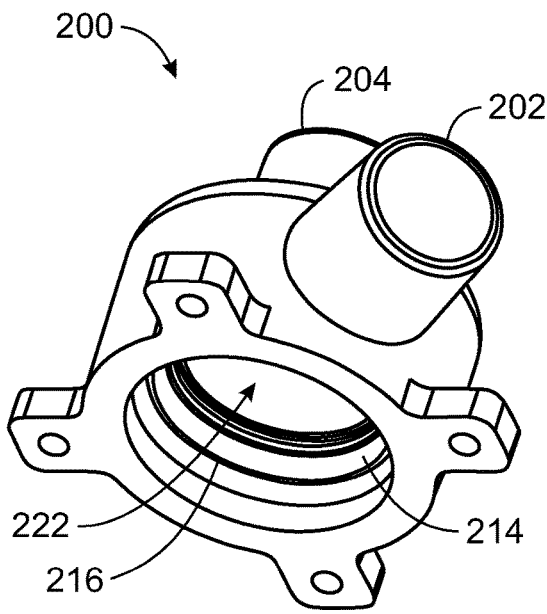
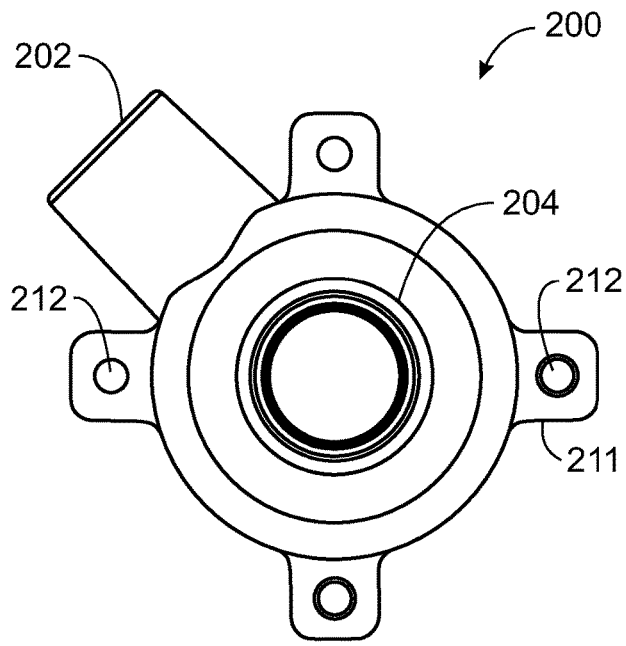
FIG. 2B
FIG. 2C
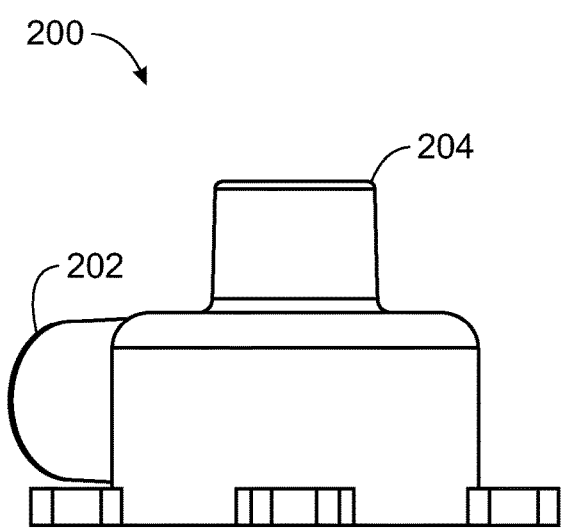
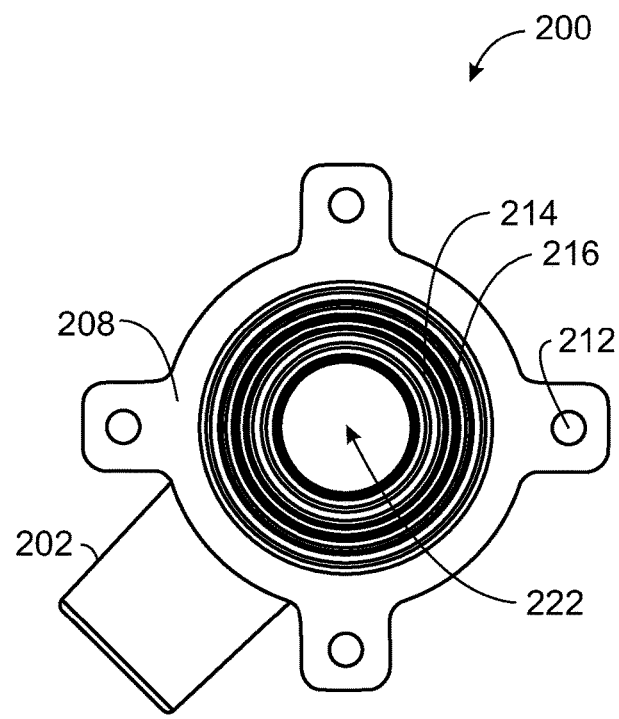
FIG. 2D
FIG. 2E

INTEGRATED DIVERTER VALVE WITH DUAL GAS PATH FOR VENTILATOR AND ANESTHESIA SYSTEMS

FIELD

Embodiments of the subject matter disclosed herein relate to a diverter valve, and in particular to a four port, two channel pneumatic flow diverter valve.

BACKGROUND

Over the course of a medical treatment, a patient may require some form of respiratory support provided by a ventilator or may require multiple different types of respiratory support which is generally provided by different types of ventilation devices in different settings. Respiratory support may include assisted breathing, wherein the ventilator detects breath attempts and provides supplemental pressure and gas flow for the patient to complete and effective respiratory cycle. Other forms of respiratory support include mechanical ventilation, whereby the ventilator also initiates the respiratory phase of each respiratory cycle.

Different types of mechanical ventilators are available that each provide mechanical ventilation for a particular setting, such as an intensive care ventilator configured to provide mechanical ventilation support for an extended duration of time and an operating room ventilator configured to provide anesthetic gas to the patient and to provide respiratory support to the patient while they are under general anesthesia. During treatment, the patient receiving respiratory support may need to be transferred between ventilator systems. As such, it is desired to have a system which provides for continuous respiratory support when incorporating additional machines having different capabilities. Further, it is desired to have a valve which provides for seamless incorporation of these additional machines without disrupting continuous airflow.

BRIEF DESCRIPTION

According to an aspect of the disclosure, the flow diversion valve may include: a valve housing having a first inlet, a second inlet, a first outlet, a second outlet, and a lower valve seat; and a check valve having a flange and tubular body, the check valve being movably disposed within the valve housing. The flow diversion valve may have a first configuration in which the check valve is in a first position to provide a first flow path from the first inlet to the first outlet. The flow diversion valve may have a second configuration in which the check valve is in a second position to provide a second flow path from the first inlet through the second outlet and a third flow path from the second inlet to the first outlet.

According to an aspect of the disclosure, the flow diversion valve may include: a valve housing having a first inlet, a second inlet, a first outlet, a second outlet, and a lower valve seat; and a check valve having a flange and tubular body, the check valve being movably disposed within the valve housing. The flow diversion valve may have a first configuration in which the check valve is in a first position to provide a first flow path from the first inlet to the first outlet. The flow diversion valve may have a second configuration in which the check valve is in a second position to provide a second flow path from the first inlet through the second outlet and a third flow path from the second inlet to the first outlet.

According to an aspect of the disclosure, a flow diversion system may include: a diversion valve including: a valve housing having a first inlet, a second inlet, a first outlet, a second outlet, and an inner cavity; a float valve provided within the inner cavity of the valve housing; and a check valve provided on the float valve; and a host adapter including: a central lumen and a concentric cavity surrounding the central lumen. The flow diversion valve may have a first configuration in which the float valve is in a closed position to provide a first flow path from the first inlet to the first outlet. The flow diversion valve may have a second configuration in which the float valve is in an open position to provide a second flow path from the first inlet through the second outlet and a third flow path from the second inlet to the first outlet. The flow diversion valve may be configured to be biased into the second position by the host adapter.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 2B shows a perspective view of the upper valve housing, according to an embodiment.

FIG. 2C shows a top view of the upper valve housing, according to an embodiment.

FIG. 2D shows a side view of the upper valve housing, according to an embodiment.

FIG. 2E shows a bottom view of the upper valve housing, according to an embodiment.

DETAILED DESCRIPTION

The following detailed description of example embodiments refers to the accompanying drawings. The same reference numbers in different drawings may identify the same or similar elements.

The foregoing disclosure provides illustration and description, but is not intended to be exhaustive or to limit the implementations to the precise form disclosed. Modifications and variations are possible in light of the below disclosure or may be acquired from practice of the implementations.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a"and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more" or "at least one." Where only one item is intended, the term "one" or similar language is used. Also, as used herein, the terms "has," "have," "having," "includes," "includes,""including," "comprises," "comprising," or the like are intended to be open-ended terms. Further, the phrase "based on" is intended to mean "based, at least in part, on"unless explicitly stated otherwise. References to "one embodiment" of the present invention are not intended to be interpreted as excluding the existence of additional embodiments that also incorporate the recited features. The terms "first," "second,"and "third," etc. are used merely as labels, and are not intended to impose numerical requirements or a particular positional order on their objects.

The following description relates to various embodiments of a diverter valve.

Figure 1A:
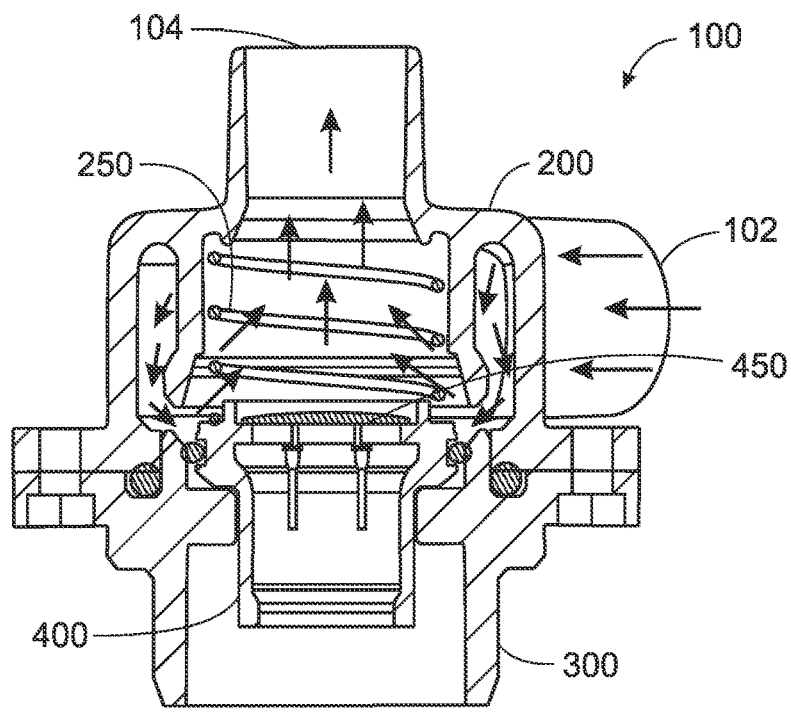
FIG. 1A is a diagram of the diverter valve in a first configuration, according to an embodiment.
Figure 1B:
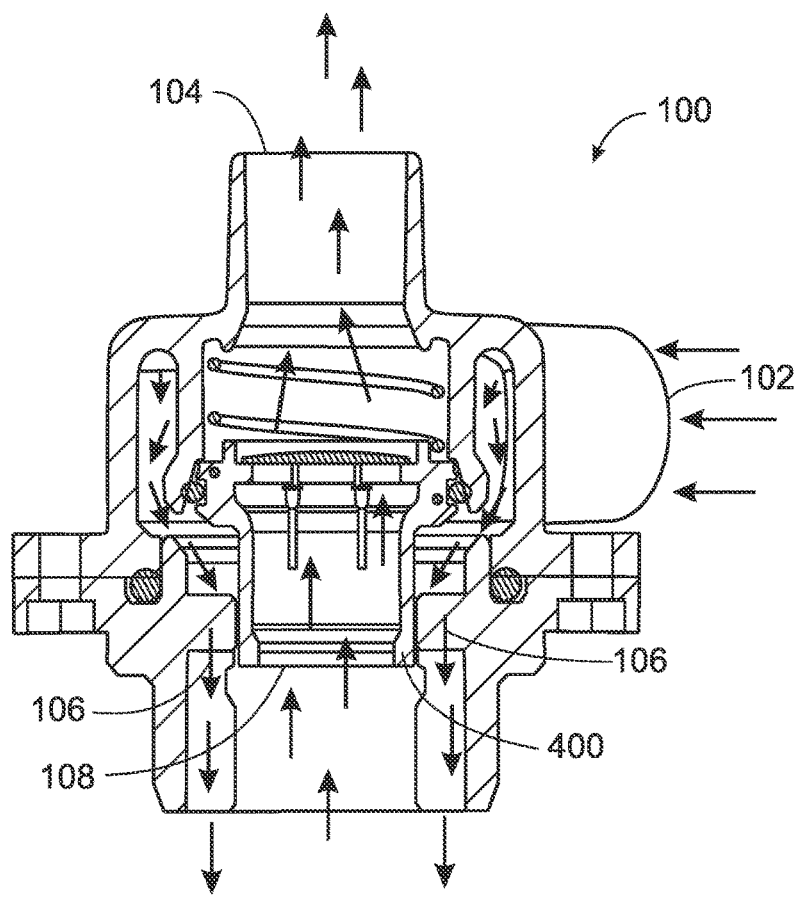
FIG. 1B is a diagram of the diverter valve in a second configuration, according to an embodiment.

FIG. 1A is a diagram of the diverter valve 100 in a first configuration, according to an embodiment. FIG. 1B is a diagram of the diverter valve 100 in a second configuration, according to an embodiment. Throughout this disclosure, the orientation of the diverter valve shown in FIGS. 1A and 1B will be used when describing the valve. For example, the top of the valve shown in FIGS. 1A and 1B will be referred to as the top or upper portion of the valve. This orientation is not meant to be limiting but is rather to clarify the explanation of the valve.

As shown in FIGS. 1A and 1B, the diverter valve 100 may include an upper valve housing 200, a lower valve housing 300, a float valve 400, a check valve 450, and a biasing member 250. The diverter valve may be held in the first configuration by the biasing member 250 which forces the float valve 400 into a lower valve seat. The diverter valve 100 may be held in the second configuration by a host adapter that biases the float valve 400 into an upper position in which the float valve 400 seated in an upper valve seat.

As shown by the arrows in FIG. 1A, the diverter valve 100 provides a first flow path between a first inlet 102 and a first outlet 104 when in the first configuration. Specifically, the first flow path extends from the first inlet 102 into a concentric cavity. The flow path then extends from the concentric cavity, through a concentric opening in the concentric cavity, and into a central cavity provided in a center of the concentric cavity. The check valve 450 and float valve 400 prevent downward flow, thus directing flow up and out of the first outlet 102.

As shown by the arrows in FIG. 1B, the diverter valve 100 provides a second flow path between the first inlet 102 and a second outlet 106 when in the second configuration. Specifically, the second flow path extends from the first inlet 102 into the concentric cavity. The flow path then extends from the concentric cavity to the second outlet 106 through openings in the lower valve seat.

As shown by the arrows in FIG. 1B, the diverter valve 100 also provides a third flow path between a second inlet 108 and the first outlet 104 when in the second configuration. The third flow path extends through the central float valve 400 and check valve 450 provided thereon, and then out through the central cavity and the first outlet 104.

The concentrically oriented flow paths provide for a compact diverter valve. By incorporating a compact diverter valve, a device, such as a portable ventilator, may be provided with a smaller, more portable size. Additionally, by having only 4 primary components, the valve may be easily manufactured and assembled. Further, the disclosed valve architecture allows for components capable of being autoclaved for reusability.

Figure 2A:
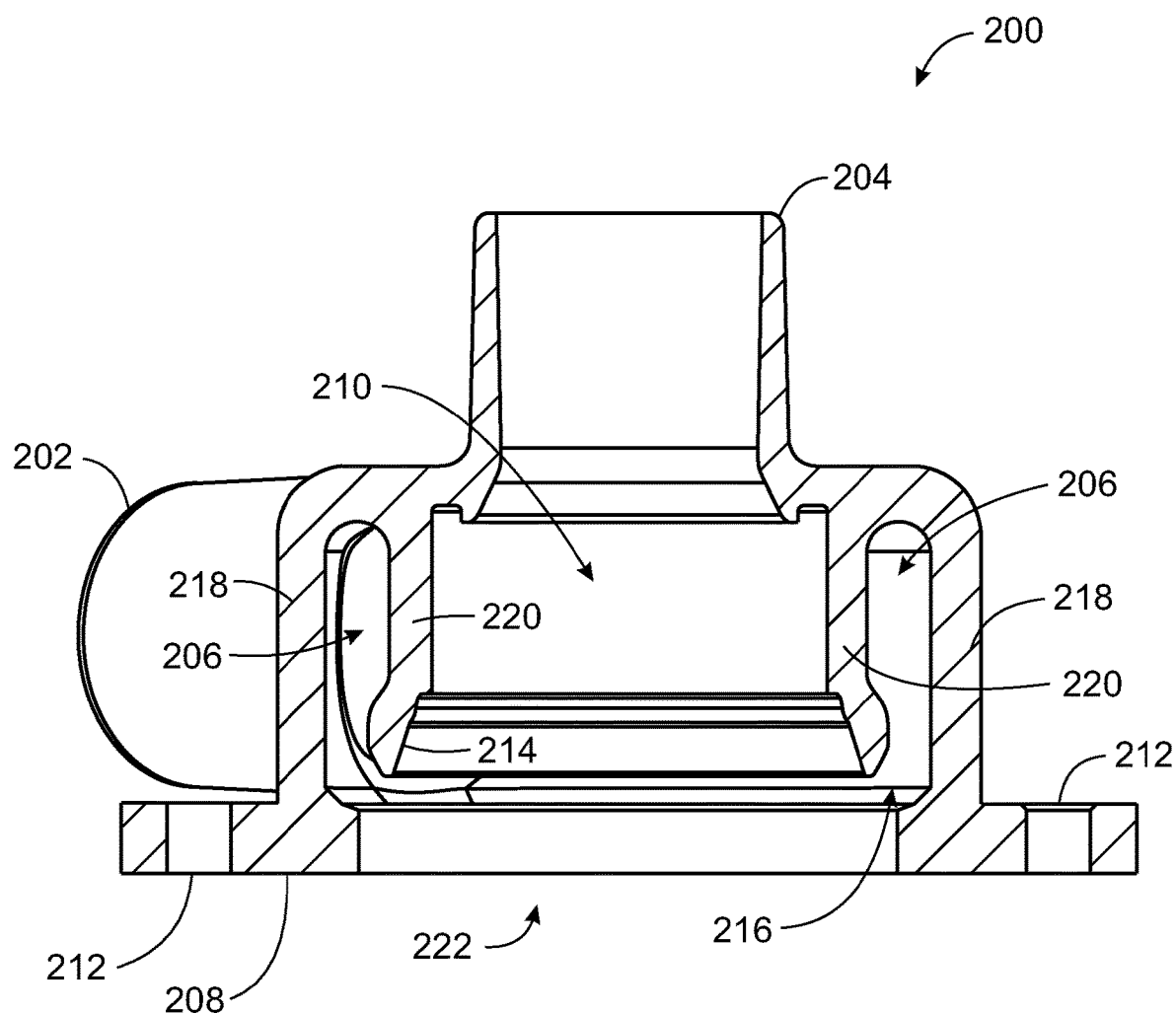
FIG. 2A shows a cross-sectional view of an upper valve housing, according to an embodiment.

FIG. 2A shows a cross-sectional view of an upper valve housing 200, according to an embodiment. FIG. 2B shows a perspective view of the upper valve housing 200, according to an embodiment. FIG. 2C shows a top view of the upper valve housing 200, according to an embodiment. FIG. 2D shows a side view of the upper valve housing 200, according to an embodiment. FIG. 2E shows a bottom view of the upper valve housing 200, according to an embodiment.

As shown in FIGS. 2A-2E, the upper valve housing 200 may include a first inlet port 202, at which a first flow path may begin. The first flow path may extend from the first inlet port 202 into a concentric cavity 206. The concentric cavity 206 may be defined by an outer wall 218 and an inner wall 220 of the upper valve housing 200. The outer wall 218 and inner wall 220 may have at least a partially tubular shape. A central cavity 210 may be defined by an inner surface of the inner wall 220.

The concentric cavity 206 and the central cavity 210 may be concentric and/or coaxial. The concentric cavity 206 may be in fluid communication with the central cavity 210 through a concentric opening 216 at the bottom of the concentric cavity 210. The inner wall 220 may have a terminal end that is separated from a lower portion of the upper valve housing 200, thus providing the concentric opening 216. A first outlet port 204 may be provided above the central cavity 210 to provide an upper outlet from the central cavity 210.

A central opening 222 may be provided below the central cavity 210. The central opening may be sized and shaped to mate with a mating flange of the lower valve housing 300.

A lower end of the inner wall 220 may define an upper valve seat 214 for accepting the float valve 400. As shown in FIG. 2A, the lower end of the inner wall 220 may flare out to accept the float valve 400. As such, the upper valve seat 214 may be sized and shaped to mate with the float valve 400 to provide a fluid tight seal (also referred to as a pneumatic seal) between a housing of the float valve 400 and the inner wall 220 of the upper valve housing 200.

A bottom surface 208 of the upper valve housing 200 may be sized and shaped to provide a fluid tight seal with the lower valve housing 300. As shown in FIG. 2A, the bottom surface 208 may be flat for creating a fluid tight seal with a gasket of the lower valve housing 300. Fastener apertures 212 may be provided in fastener protrusions 211 of the upper valve housing 200 for securing the upper valve housing 200 to the lower valve housing 300 using fasteners such as screws or bolts. The fasteners may be removable to provide for disassembly and cleaning of the diverter valve 100. Attachment of the upper housing 200 and the lower housing 300 using fasteners and apertures is a non-limiting embodiment. According to other embodiments, the upper housing 200 may be secured to the lower housing 300 through other methods known in the art. For example, the upper housing 200 and the lower housing 300 may be attached using a rotate and lock technique.

Figure 3A:
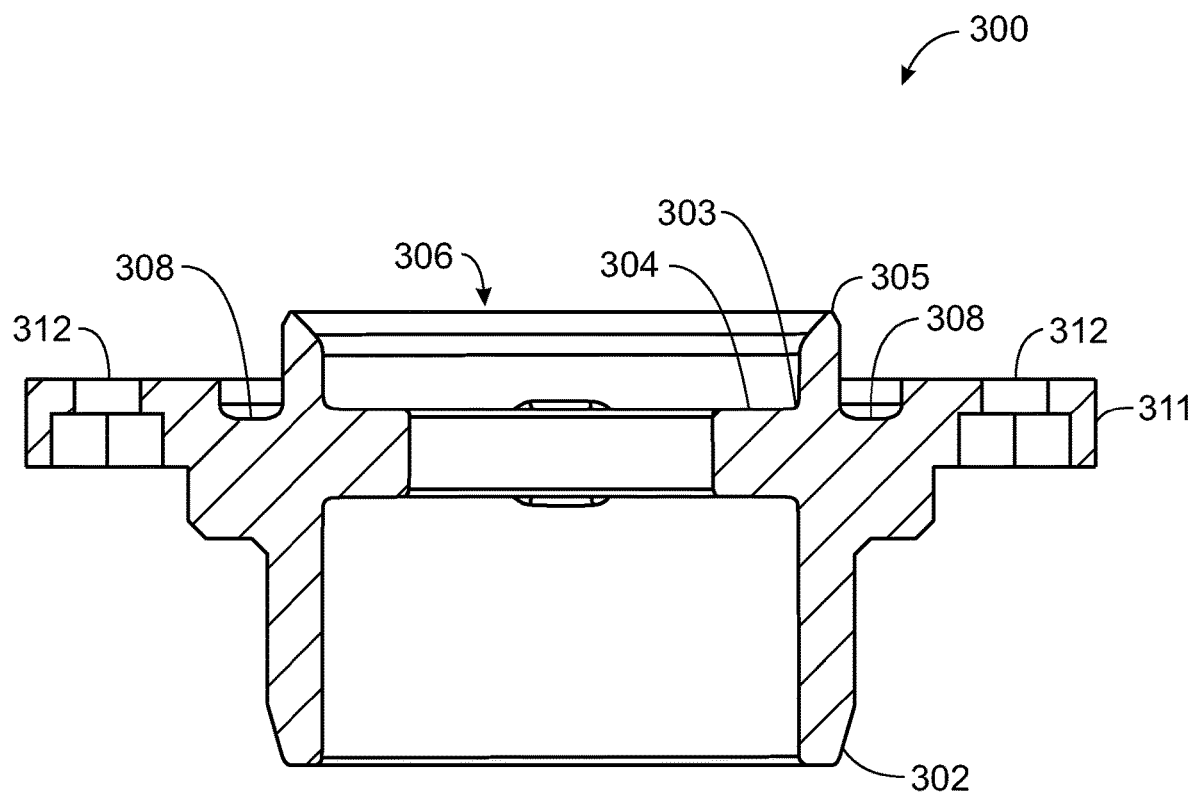
FIG. 3A shows a cross-sectional view of a lower valve housing, according to an embodiment.
Figure 3B:
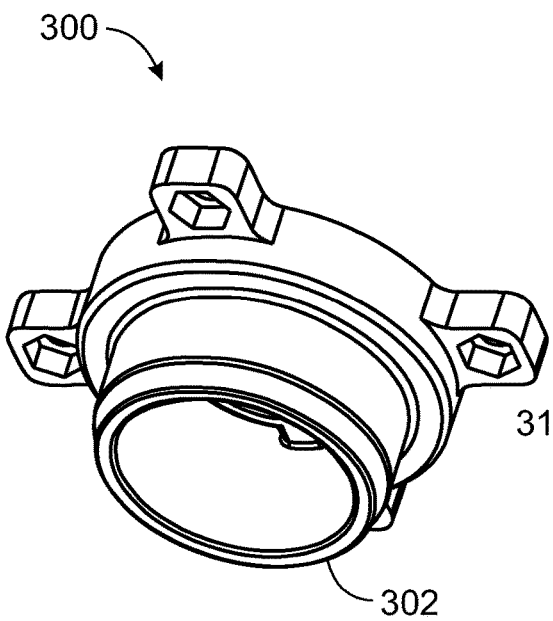
FIG. 3B shows a perspective view of the lower valve housing, according to an embodiment.
Figure 3C:
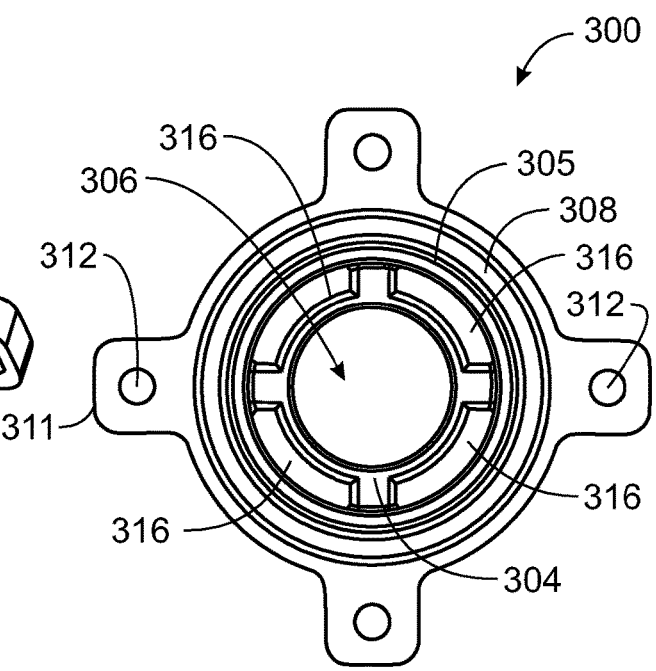
FIG. 3C shows a top view of the lower valve housing, according to an embodiment.
Figure 3D:
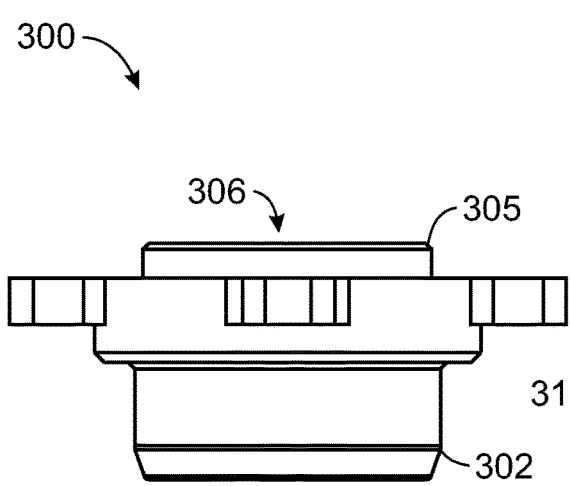
FIG. 3D shows a side view of the lower valve housing, according to an embodiment.
Figure 3E:
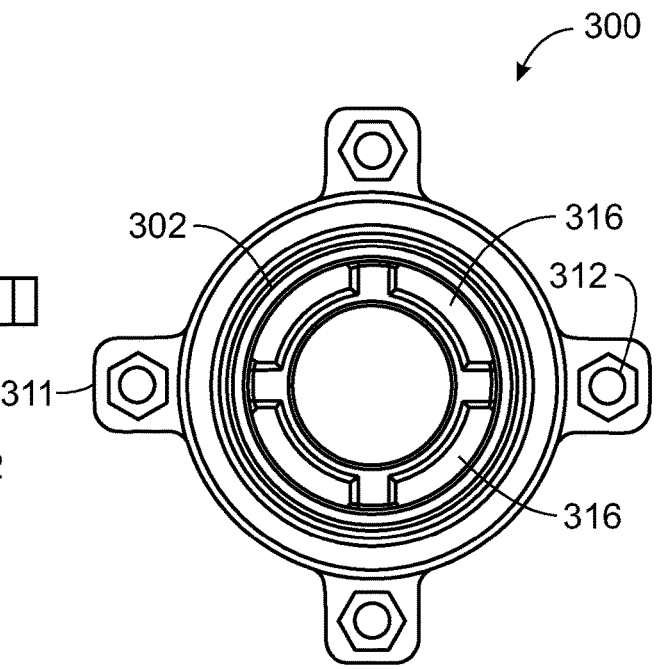
FIG. 3E shows a bottom view of the lower valve housing, according to an embodiment.

FIG. 3A shows a cross-sectional view of a lower valve housing 300, according to an embodiment. FIG. 3B shows a perspective view of the lower valve housing 300, according to an embodiment. FIG. 3C shows a top view of the lower valve housing 300, according to an embodiment. FIG. 3D shows a side view of the lower valve housing 300, according to an embodiment. FIG. 3E shows a bottom view of the lower valve housing 300, according to an embodiment.

As shown in FIGS. 3A-E, the lower valve housing 300 may provide a central opening 306. A lower portion of the central opening 306 may be defined by a receiving port 302. The receiving port 302 may include a cylindrical flange protruding downward from lower valve housing 300. An upper portion of the central aperture 306 may be defined by a lower valve seat 303 for seating the float valve 400 when the diverter valve 100 is in the first configuration.

The lower valve seat 303 may include an inward protruding flange 304 encircling the central opening 306. The inward protruding flange 304 may have an inner diameter sized and shaped to match a size and shape of a body of the float valve 400 and an outer diameter larger than a seating flange of the float valve 400. A mating flange 305 may extend up from the lower valve seat 303 and encircle the central opening 306. The mating flange 305 may be sized and shaped to mate with a lower portion of the central opening 222 of the upper valve housing 200 (see FIGS. 6A-6B). An inner surface of the mating flange 305 may be sized and shaped to mate with the float valve 400 to create a fluid tight seal between the float valve 400 and the lower valve housing 300 when the float valve 400 is in the second configuration.

Outlet apertures 316 may extend through the inward protruding flange 304 to provide the second outlet 106. When the float valve 400 is in a raised position (e.g. second configuration), the outlet apertures 316 may provide for fluid flow from the concentric cavity 206 of the upper valve housing 200 to the receiving port 302 of the lower valve housing 300. When the float valve is in the lowered position (e.g. first configuration), the outlet apertures 316 may be sealed by the float valve 400, thus preventing fluid flow from the concentric cavity 206 to the receiving port 302.

A gasket groove 308 may be provided in an upper surface of the lower valve housing 300 for holding a gasket that seals with the upper valve housing 200 when the two are mated. For example, O-ring 602 may be disposed within the gasket groove 308 (see FIGS. 6A-6B).

Fastener apertures 312 may be provided in protrusions 311 that extend out from the lower valve housing 300. The protrusions 311 may be sized and shaped to match the protrusions 211 of the upper valve housing 200. The fastener apertures 312 of the lower valve housing 300 may be sized and shaped to match the fastener apertures 212 of the upper valve housing 200. Fasteners may extend through the fastener apertures 212 of the upper valve housing 200 and the fastener apertures 312 of the lower valve housing 300 to secure the upper valve housing 200 and lower valve housing 300 together. The user of fasteners and fastener apertures 212 and 312 to connect the upper housing 200 and the lower housing 300 is described as a non-limiting embodiment. According to other embodiments, the upper housing 200 and the lower housing 300 may be connected using other features known in the art.

Figure 6A:
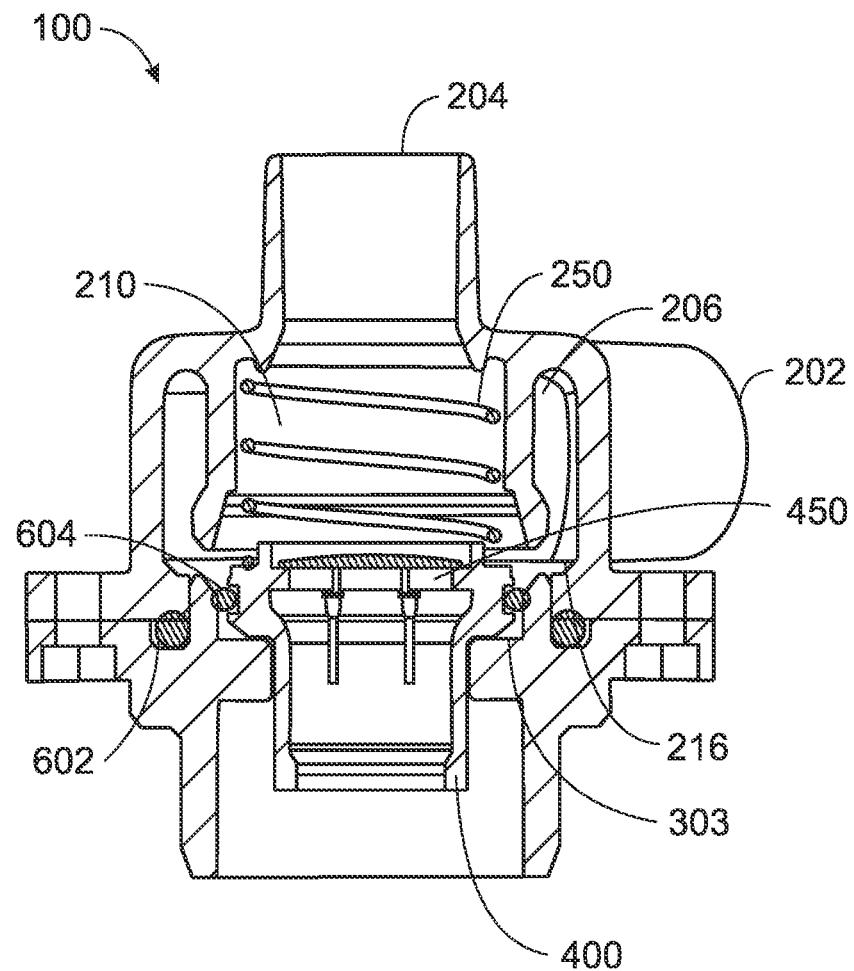
FIG. 6A shows the first configuration of the diverter valve in which the float valve is in a lowered position to provide the first flow path, according to an embodiment.
Figure 6B:
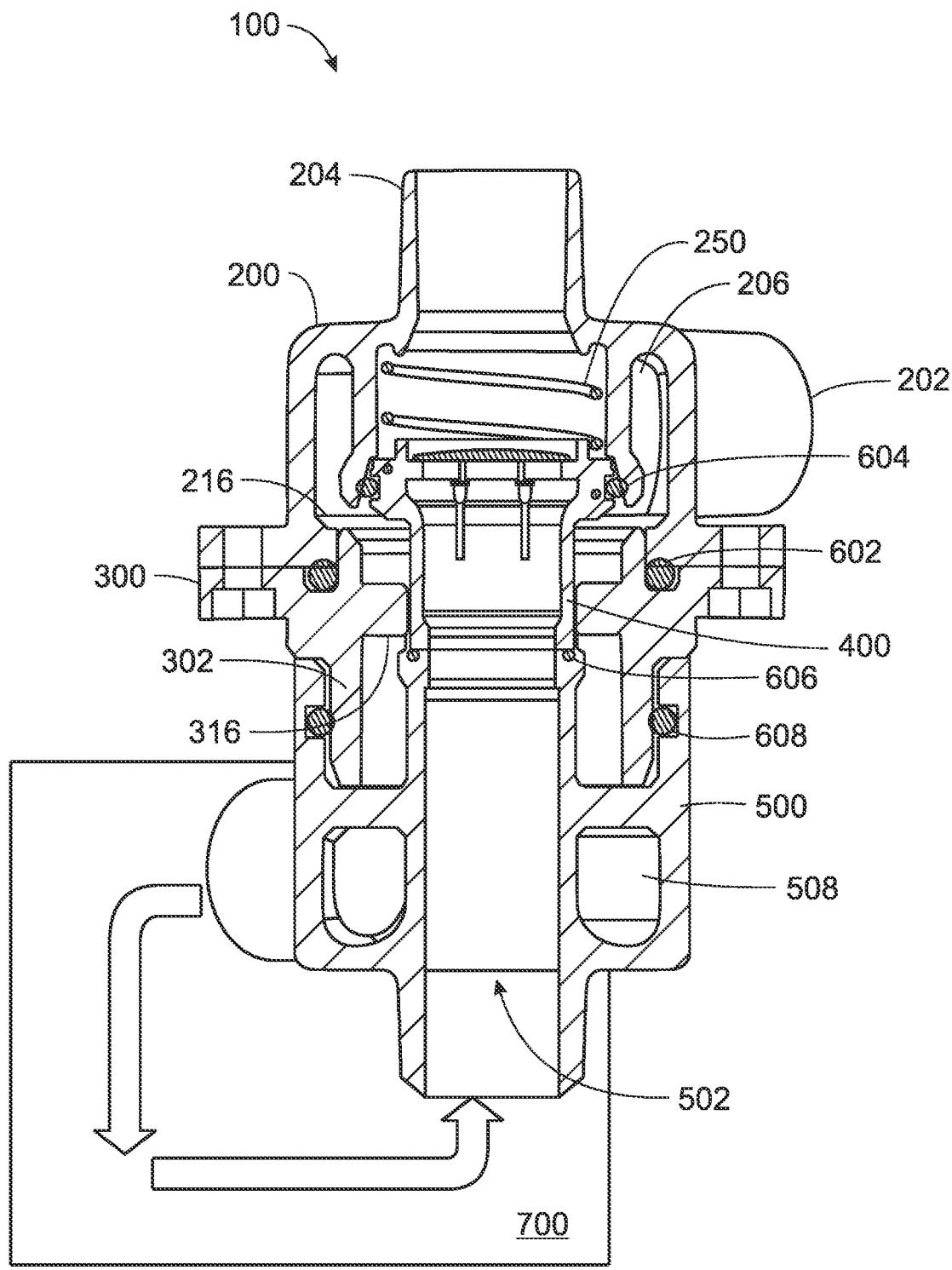
FIG. 6B shows the second configuration of the diverter valve in which the float valve is in a raised position to provide second and third flow paths, according to an embodiment.

The receiving port 302 may be sized and shaped to mate with a host adapter 500 (see FIG. 6B). An outer surface of the receiving port 302 may be sized and shaped to create a fluid tight seal with an outer flange of the host adapter 500. An inner surface of the receiving port 302 may be sized to receive an inner wall 504 of the host adapter 500 while providing space around an outside of the inner wall 404 for fluid flow from the outlet apertures 316 to enter the host adapter 500.

Figure 4A:
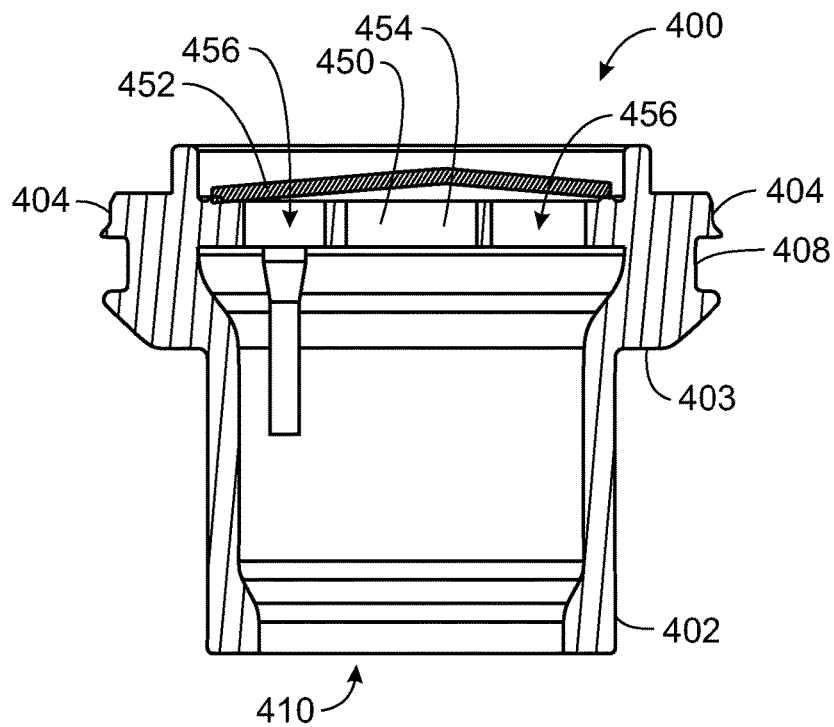
FIG. 4A shows a cross-sectional view of a float valve, according to an embodiment.
Figure 4B:
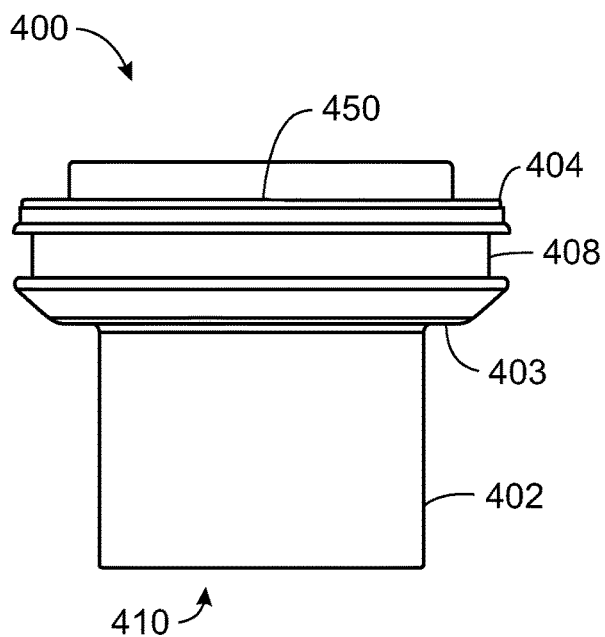
FIG. 4B shows a side view of the float valve, according to an embodiment.
Figure 4C:
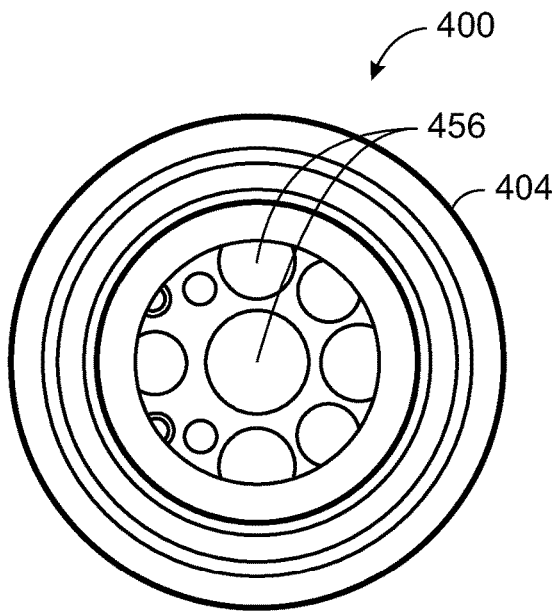
FIG. 4C shows a bottom view of the float valve, according to an embodiment.

FIG. 4A shows a cross-sectional view of a float valve 400, according to an embodiment. FIG. 4B shows a side view of the float valve 400, according to an embodiment. FIG. 4C shows a bottom view of the float valve 400, according to an embodiment.

As shown in FIGS. 4A-4C, the float valve 400 may define a central lumen 410 extending from a lower end of the float valve 400 to a check valve 450. The check valve 450 may prevent fluid flow in the downward direction while allowing fluid flow in the upward direction. For example, fluid flowing up through the central lumen 410 may pass through the check valve 450 while fluid flowing in from above the check valve 450 will be blocked from flowing into the central lumen 410.

According to the non-limiting embodiment shown in FIGS. 4A-4C, the check valve 450 may include a valve flap 452 provided on a valve support 454. The valve support 454 may have one or more opening 456 to allow fluid to flow therethrough. When a greater fluid pressure is provided below the check valve 450, the valve flap 452 may be push away from the valve support 454, thus allowing forward fluid flow though the openings 456. When a greater fluid pressure is provided above the check valve 450, the valve flap 452 may be pressed against the valve support 454, thus sealing the openings 456 and preventing reverse fluid flow. According to other embodiment, other types of check valves may be used. That is, any valve or structure that prevents fluid flow in one direction while allowing fluid flow in the opposing direction may be used as check valve 450.

A valve seating flange 404 may protrude outward from a tubular body 402 of the float valve 400. The valve seating flange 404 may be sized and shaped to mate with the lower valve seat 303 of the lower valve housing 300 and the upper valve seat 214 of the upper valve housing 200. A lower surface 403 of the valve seating flange 404 may be sized and shaped to mate with an upper surface of the inward protruding flange 304 of the lower valve seat 303 of the lower valve housing 300. The valve seating flange may have a gasket groove 408 for retaining a gasket, such as O-ring 604 (see FIGS. 6A-6B). The gasket retaining groove 408 may be sized and shaped to hold a gasket in a position to create a liquid tight seal between the valve seating flange 404 and the lower valve seat 303 of the lower valve housing 300 when the diverter valve 100 is in the first configuration. The gasket retaining groove 408 may also be sized and shaped to hold a gasket in a position to create a liquid tight seal between the valve seating flange 404 and the upper valve seat 214 of the upper valve housing 200 when the diverter valve 100 is in the second configuration.

Figure 5A:
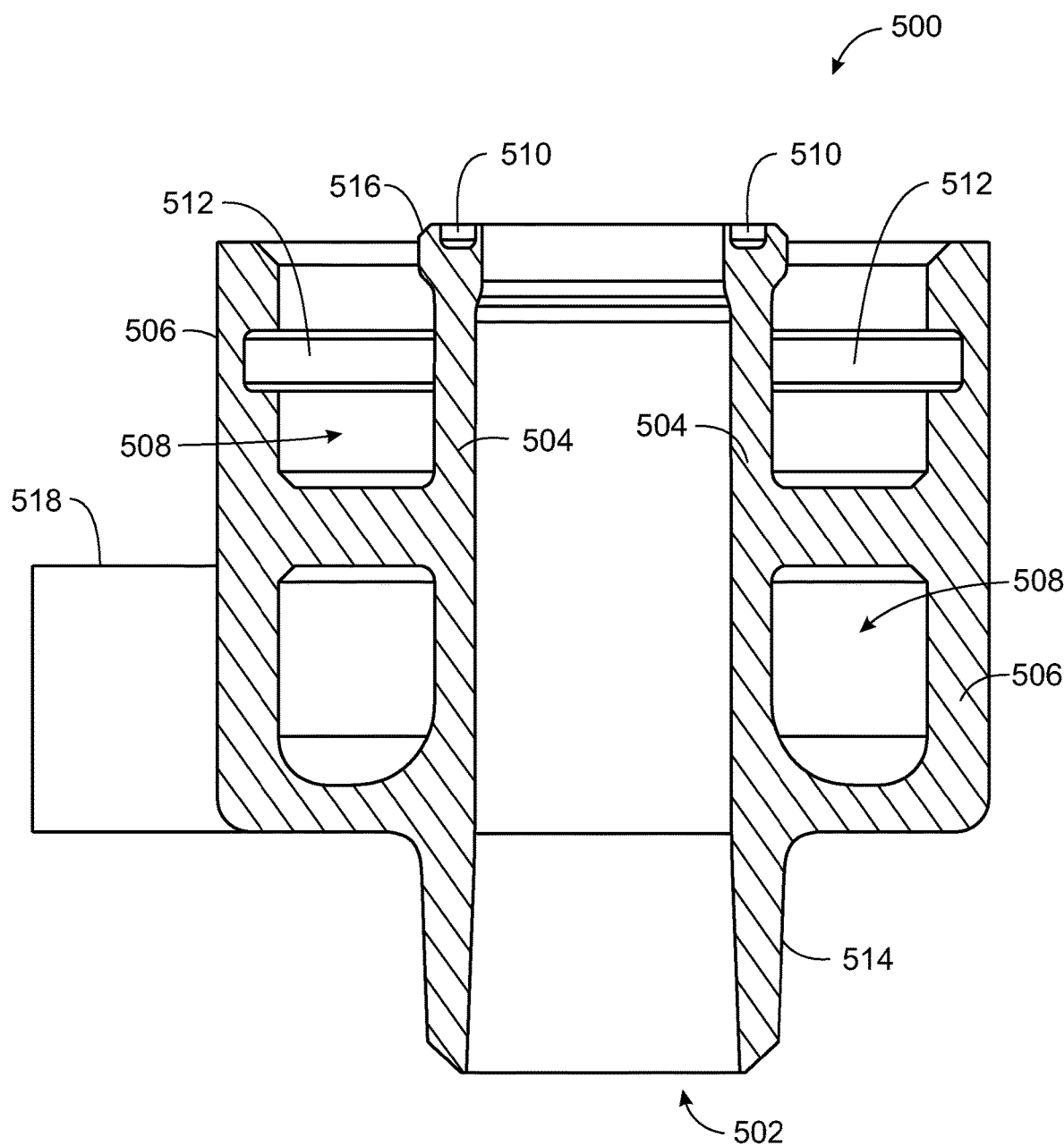
FIG. 5A shows a cross-sectional view of a host adapter, according to an embodiment.
Figure 5B:
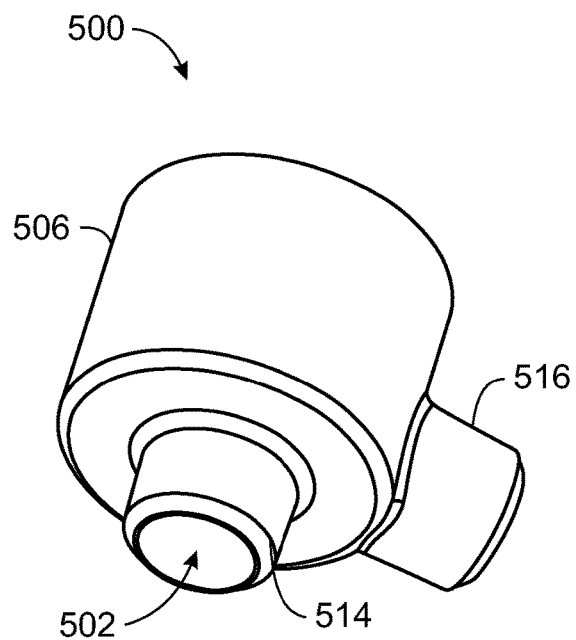
FIG. 5B shows a perspective view of the host adapter, according to an embodiment.
Figure 5C:
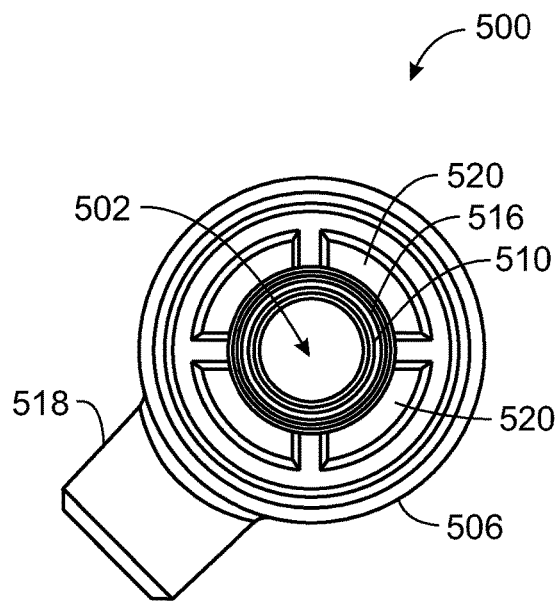
FIG. 5C shows a top view of the host adapter, according to an embodiment.
Figure 5D:
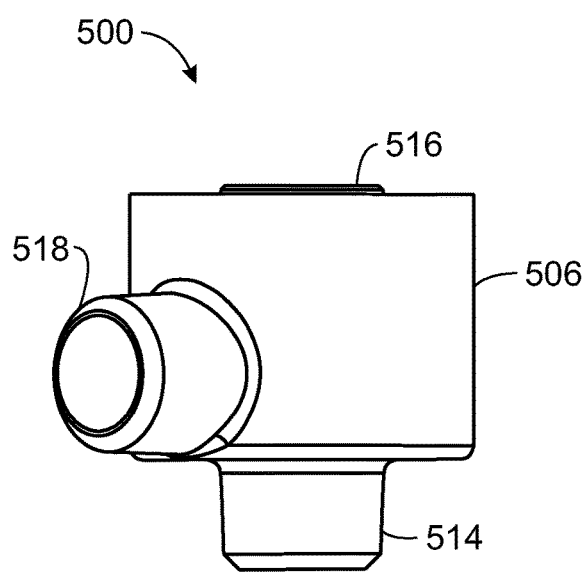
FIG. 5D shows a side view of the host adapter, according to an embodiment.
Figure 5E:
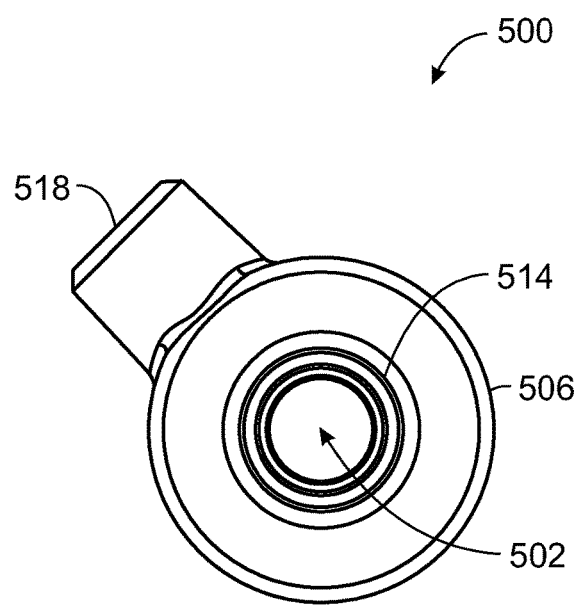
FIG. 5E shows a bottom view of the host adapter, according to an embodiment.

FIG. 5A shows a cross-sectional view of a host adapter 500, according to an embodiment. FIG. 5B shows a perspective view of the host adapter 500, according to an embodiment. FIG. 5C shows a top view of the host adapter 500, according to an embodiment. FIG. 5D shows a side view of the host adapter 500, according to an embodiment. FIG. 5E shows a bottom view of the host adapter 500, according to an embodiment.

As shown in FIGS. 5A-5E, the host adapter 500 may include an inner wall 504 and an outer wall 506. The inner wall 504 and the outer wall 506 may have tubular shapes which are concentrically oriented. The inner wall 504 may define a central lumen 502. An upper end of the inner wall 504 may define a plunger 516. The plunger 516 may be sized and shaped to mate with a lower edge of the float valve 400. As shown in FIG. 6B, the host adapter 500 may push the float valve 400 into the second configuration by engaging the plunger 516 of the host adapter 500 with the float valve 400. A gasket groove 510 may be provided in the plunger 516 to retain a gasket, such as O-ring 606 (see FIGS. 6A-6B), for obtaining a fluid tight seal between the host adapter 500 and the float valve 400.

A concentric cavity 508 may be provided between the inner wall 504 and the outer wall 506. The concentric cavity 508 may be in fluid communication with inlet openings 520 and an outlet port 518 of the host adapter 500. A gasket groove 512 may be provided on an inner surface of the outer wall 506 to retain a gasket, such as O-ring 608 (see FIGS. 6A-6B), for obtaining a fluid tight seal between the outer wall 506 and the receiving port 302 of the lower valve housing 300.

FIG. 6A shows the first configuration of the diverter valve 100 in which the float valve 400 is in a lowered position (e.g. first configuration) to provide the first flow path, according to an embodiment. As shown in FIG. 6A, the float valve 400 may be forced into the lower position by a biasing member, such as coiled spring 250. However, the depicted coil spring is not intended to be limiting, and other known biasing members may be used.

The first flow path may extend from the first inlet port 202 into the concentric cavity 206 of the upper valve housing 200. The first flow path may then extend through the concentric opening 216 into the central cavity 210 and out of the first outlet port 204. As shown in FIG. 6A, the float valve 400 being seated in the lower valve seat 303 and the check valve 450 preventing downwards flow causes the first flow path to exit the diverter valve 100 through the first outlet port 204 without entering the host adapter 500.

FIG. 6B shows the second configuration of the diverter valve 100 in which the float valve 400 is in a raised position (e.g. second configuration) to provide second and third flow paths, according to an embodiment. As shown in FIG. 6B, the float valve 400 may be forced into the upper position by a host adapter 500.

As shown in FIG. 6B, the second flow path extends from the first inlet port 202 into the concentric cavity 206 of the upper valve housing 200. The second flow path then extends through the concentric opening 216 of the upper valve housing 200 and into the outlet apertures 316 of the lower valve housing 300. As shown in FIG. 6B, when the host adapter 500 is engaged with the diverter valve 100, the second flow path may exit from the receiving port 302 of the diverter valve 100, and then flows into the concentric cavity 508 and out of the outlet port 518 of the host adapter 500.

As shown in FIG. 6B, the third flow path of the diverter valve 100 may extend up through the central lumen 502 of the host device 500, the body 402 of the float valve 400, and the check valve 450. Once through the check valve 450, the third flow path may extend into the central cavity 210 of the upper valve housing 200, and out of the first outlet port 204.

According to an example, the diversion valve may be connected to a portable ventilator and the host adapter may be connected to a host device. When the portable ventilator is not docked with the host device, the portable ventilator provides medical gas directly to an outlet of the portable ventilator. In some cases, it may be desired to provide additional control over the flowed medical gas. For example, it may be desired to control temperature and humidity of the medical gas. It may also be desired to flow the medical gas at a rate which is higher than a rate at which the portable ventilator can provide or add medications to the medical gas. When the portable ventilator is unable to provide these additional services, it may be docked with a host device 700 that is capable of providing these features. Accordingly, the first fluid flow path provided by the first configuration of the diverter valve may be used in the undocked configuration in which the portable ventilator is provide direct flow to a patient.

When the portable ventilator is docked to the host device 700 including the host adapter 500, the second fluid flow path provided by the second configuration of the diverter valve, may flow the medical gas provided by the portable ventilator into the host device 700 which provides additional services to the medical gas. The serviced medical gas may then flow out of the host device 700 into the third flow path provided by the diverter valve 100 which outputs to an outlet of the portable ventilator. Using the diverter valve 100, continuous respiratory support may be provided to a patient while incorporate devices having different capabilities.

The above example embodiments describe tubular/circular shaped diverter valves. However, these shapes are not intended to be limiting. For example, the shape of the valve from the top view may be circular (as shown in the example embodiments), square, rectangular or other shapes based on the use of the valve. For example, the valve may be sized to fit with a cavity of a device using the valve.

According to an aspect of the disclosure, the flow diversion valve may include: a valve housing having a first inlet, a second inlet, a first outlet, a second outlet, and a lower valve seat; and a check valve having a flange and tubular body, the check valve being movably disposed within the valve housing. The flow diversion valve may have a first configuration in which the check valve is in a first position to provide a first flow path from the first inlet to the first outlet. The flow diversion valve may have a second configuration in which the check valve is in a second position to provide a second flow path from the first inlet through the second outlet and a third flow path from the second inlet to the first outlet.

According to an aspect of the disclosure, in the first configuration, the flange of the check valve may be seated in the lower valve seat, and in the second configuration, the flange of the check valve is spaced apart from the lower valve seat.

According to an aspect of the disclosure, a liquid tight seal may be formed between the lower valve seat and the check valve when the check valve is in the first position.

According to an aspect of the disclosure, the valve housing may further include an upper valve seat, and a liquid tight seal may be formed between the upper valve seat and the check valve when the check valve is in the second position.

According to an aspect of the disclosure, the check valve may have a flow direction and an opposite antiflow direction. The first flow path may engage the check valve in the antiflow direction and the third flow path may engage the check valve in the flow direction.

According to an aspect of the disclosure, the check valve may be biased towards the first position by a biasing member.

According to an aspect of the disclosure, the check valve may be configured to be biased towards the second position by engaging a host device having an inlet that mates with the second inlet.

According to an aspect of the disclosure, the second outlet may be concentric to the second inlet.

According to an aspect of the disclosure, the valve seat may be provided between the second inlet and the first outlet.

According to an aspect of the disclosure, the second outlet may include at least one aperture in the lower valve seat, and wherein the second outlet is sealed shut when the fluid diversion valve is in the first configuration.

According to an aspect of the disclosure, the second flow path and the third flow path may be concentrically oriented.

According to an aspect of the disclosure, the second flow path and the third flow path may be coaxially aligned.

According to an aspect of the disclosure, the flow diversion valve may include: a valve housing having a first inlet, a second inlet, a first outlet, a second outlet, and a lower valve seat; and a check valve having a flange and tubular body, the check valve being movably disposed within the valve housing. The flow diversion valve may have a first configuration in which the check valve is in a first position to provide a first flow path from the first inlet to the first outlet. The flow diversion valve may have a second configuration in which the check valve is in a second position to provide a second flow path from the first inlet through the second outlet and a third flow path from the second inlet to the first outlet.

According to an aspect of the disclosure, the valve housing may further include a lower valve seat. In the first configuration, float valve may be seated in the lower valve seat, and in the second configuration, the float valve is spaced apart from the lower valve seat.

According to an aspect of the disclosure, the second outlet may include at least one aperture in the lower valve seat.

According to an aspect of the disclosure, the check valve may have a flow direction and an opposite antiflow direction, wherein the first flow path engages the check valve in the antiflow direction and the third flow path engage the check valve in the flow direction.

According to an aspect of the disclosure, the second flow path and the third flow path may be concentrically oriented.

According to an aspect of the disclosure, a flow diversion system may include: a diversion valve including: a valve housing having a first inlet, a second inlet, a first outlet, a second outlet, and an inner cavity; a float valve provided within the inner cavity of the valve housing; and a check valve provided on the float valve; and a host adapter including: a central lumen and a concentric cavity surrounding the central lumen. The flow diversion valve may have a first configuration in which the float valve is in a closed position to provide a first flow path from the first inlet to the first outlet. The flow diversion valve may have a second configuration in which the float valve is in an open position to provide a second flow path from the first inlet through the second outlet and a third flow path from the second inlet to the first outlet. The flow diversion valve may be configured to be biased into the second position by the host adapter.

According to an aspect of the disclosure, the central lumen of the host adapter is configured to provide a fluid tight seal with the float valve.

According to an aspect of the disclosure, an upper edge of the central lumen may be sized and shaped to mate with a lower edge of the float valve.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A flow diversion valve comprising:
a valve housing having a first inlet, a second inlet, a first outlet, a second outlet, and a lower valve seat; and
a check valve having a flange and tubular body, the check valve being movably disposed within the valve housing,
wherein the flow diversion valve has a first configuration in which the check valve is in a first position to provide a first flow path from the first inlet to the first outlet, and
wherein the flow diversion valve has a second configuration in which the check valve is in a second position to provide a second flow path from the first inlet through the second outlet and a third flow path from the second inlet to the first outlet.

2. The flow diversion valve of claim 1, wherein, in the first configuration, the flange of the check valve is seated in the lower valve seat, and in the second configuration, the flange of the check valve is spaced apart from the lower valve seat.

3. The flow diversion valve of claim 2, wherein a liquid tight seal is formed between the lower valve seat and the check valve when the check valve is in the first position.

4. The flow diversion valve of claim 3, wherein the valve housing further comprises an upper valve seat, and wherein a liquid tight seal is formed between the upper valve seat and the check valve when the check valve is in the second position.

5. The flow diversion valve of claim 1, wherein the check valve has a flow direction and an opposite antiflow direction, wherein the first flow path engages the check valve in the antiflow direction and the third flow path engage the check valve in the flow direction.

6. The flow diversion valve of claim 1, wherein the check valve is biased towards the first position by a biasing member.

7. The flow diversion valve of claim 6, wherein the check valve is configured to be biased towards the second position by engaging a host device having an inlet that mates with the second inlet.

8. The flow diversion valve of claim 1, wherein the second outlet is concentric to the second inlet.

9. The flow diversion valve of claim 1, wherein the lower valve seat is provided between the second inlet and the first outlet.

10. The flow diversion valve of claim 1, wherein the second outlet comprises at least one aperture in the lower valve seat, and wherein the second outlet is sealed shut when the fluid diversion valve is in the first configuration.

11. The flow diversion valve of claim 1, wherein the second flow path and the third flow path are concentrically oriented.

12. The flow diversion valve of claim 1, wherein the second flow path and the third flow path are coaxially aligned.

13. A flow diversion valve comprising:
a valve housing having a first inlet, a second inlet, a first outlet, a second outlet, and an inner cavity;
a float valve provided within the inner cavity of the valve housing; and
a check valve provided on the float valve;
wherein the flow diversion valve has a first configuration in which the float valve is in a closed position to provide a first flow path from the first inlet to the first outlet, and
wherein the flow diversion valve has a second configuration in which the float valve is in an open position to provide a second flow path from the first inlet through the second outlet and a third flow path from the second inlet to the first outlet.

14. The flow diversion valve of claim 13, wherein the valve housing further comprises a lower valve seat and a upper valve seat,
wherein, in the first configuration, float valve is seated in the lower valve seat, and in the second configuration, the float valve is spaced apart from the lower valve seat and seated in the upper valve seat.

15. The flow diversion valve of claim 14, wherein the second outlet comprises at least one aperture in the lower valve seat.

16. The flow diversion valve of claim 13, wherein the check valve has a flow direction and an opposite antiflow direction, wherein the first flow path engages the check valve in the antiflow direction and the third flow path engage the check valve in the flow direction.

17. The flow diversion valve of claim 13, wherein the second flow path and the third flow path are concentrically oriented.

18. A flow diversion system comprising:
a diversion valve comprising:
a valve housing having a first inlet, a second inlet, a first outlet, a second outlet, and an inner cavity;
a float valve provided within the inner cavity of the valve housing; and
a check valve provided on the float valve; and
a host adapter comprising: a central lumen and a concentric cavity surrounding the central lumen;
wherein the flow diversion valve has a first configuration in which the float valve is in a closed position to provide a first flow path from the first inlet to the first outlet,
wherein the flow diversion valve has a second configuration in which the float valve is in an open position to provide a second flow path from the first inlet through the second outlet and a third flow path from the second inlet to the first outlet, and
wherein the flow diversion valve is configured to be biased into the second position by the host adapter.

19. The flow diversion system of claim 18, wherein the central lumen of the host adapter is configured to provide a fluid tight seal with the float valve.

20. The flow diversion system of claim 19, wherein an upper edge of the central lumen is sized and shaped to mate with a lower edge of the float valve.

* * * * *